US005683352A

United States Patent [19]

Watts

[11] Patent Number: 5,683,352

[45] Date of Patent: Nov. 4, 1997

[54] ELONGATED LOOP FOR SELF ADMINISTERED

[76] Inventor: Dempsey Watts, 1829 Courtland Dr., Lexington, Ky. 40505

[21] Appl. No.: 445,483

[22] Filed: May 22, 1995

[51] Int. Cl.$^6$ .............................. A61B 17/00; A61H 7/00

[52] U.S. Cl. ........................... 601/135; 601/137; 606/204

[58] Field of Search ............................... 606/204, 204.15, 606/201, 237, 238; 601/134–137, 128, 129, 84

[56] References Cited

U.S. PATENT DOCUMENTS

| | | | |
|---|---|---|---|
| 737,473 | 8/1903 | Porter | 606/204 |
| 1,424,884 | 8/1922 | Deane | 606/237 |
| 1,612,343 | 12/1926 | Amussen | 601/135 |
| 2,310,804 | 2/1943 | Morrison | 601/133 X |
| 2,339,572 | 1/1944 | Jurovaty | 606/204.15 |
| 2,482,838 | 9/1949 | Carlson | 601/136 |
| 4,483,328 | 11/1984 | Wolocko | 601/135 |
| 4,520,798 | 6/1985 | Lewis | 606/204 |
| 4,549,536 | 10/1985 | Varjabedian | 606/204 X |
| 5,117,815 | 6/1992 | Gentry et al. | 601/138 X |
| 5,366,475 | 11/1994 | Voss et al. | 606/204 |
| 5,560,746 | 10/1996 | Willow | 601/135 |

FOREIGN PATENT DOCUMENTS

| | | | |
|---|---|---|---|
| 2703315 | 7/1978 | Germany | 606/204 |
| 8100202 | 2/1981 | WIPO | 606/204 |

OTHER PUBLICATIONS

Prudden, "The Shepherd's Crook", brochure 1994, Bonnie Prudden Pain Erasure–1994.

*Primary Examiner*—Danton D. DeMille
*Attorney, Agent, or Firm*—Jack E. Toliver

[57] ABSTRACT

An apparatus and method for self-administered physiotherapeutic treatment and exercise of the human body in which an elongated loop shaped bar has a first distal end portion connected by a curvilinear portion to a straight portion on one side of the loop to a second curvilinear portion in a second distal end portion defining a gap wide enough to accommodate a portion of the user's body which can be remotely manipulated by the user from another part of the bar.

2 Claims, 1 Drawing Sheet

ELONGATED LOOP FOR SELF ADMINISTERED

The present invention pertains to the art of physiotherapy and primarily to an apparatus and method of therapy of the musculoskeletal structure.

BACKGROUND OF THE INVENTION

The human spinal column is a complex series of bones or vertebrae, comprising the axial skeleton of the body. The vertebrae in the lumbar region, the lower five bones above the sacrum, form the lower back. These vertebrae are often associated with low back syndrome. The cause is somewhat controversial. The pathogenesis of low back syndrome may be a degenerative disease of the spine producing chronic low back pain. Abnormal expansion, distortion and even rupture of a disc between the vertebrae due to a physical trauma, such as lifting a weight at an inappropriate angle, or by an accident, may give rise to chronic low back syndrome. Patients may experience low back syndrome from driving long distances or sitting for long periods in cramped airplane seats. In acute cases, pain from pinched nerve rootendings may radiate into the hip, or may be accompanied by episodes of shooting pain down the leg, referred to as sciatic pain. It is estimated that more than seventy five percent of the population will have significant episodes of low back syndrome. Severe nucleus pulposus rupture (disc rupture) occurs when the disc annulus, or annulus fibrosus, protrudes past the posterior longitudinal ligament to press against the nerve root endings on one side or the other of the vertebral column. A herniated nucleus pulposus (HNP) of this type can result in a distortion of the vertebral column in the region of the HNP. The large muscles of the back, the paraspinalis muscles, may go into spasm which is itself painful, but may act to take pressure off of the herniated disc by opening up the vertebral disc space on the opposite side. Spasms will usually be found on the side opposite the herniation, but not always. In the case of auxiliary herniations, where the nerve root ending is lifted up on one side, spasms on that side tends to rotate the nerve down and away from the herniating disc. Pain also may be due to inflammatory changes, muscle strain, fatigue or degenerative disease of the spine. Hence the pathogenesis of low back syndrome is controversial and difficult to diagnose.

At the opposite end of the vertebral column, the first seven vertebrae of the cervical region are often exposed to trauma related usually to a patient being involved in a rear end automobile collision. Treatment may involve wearing a neck brace and periodic visits to a physician or chiropractor. Whiplash injury claims account for one of the largest categories of insurance recovery according to the automobile insurance industry.

The thoracic region, or middle of the vertebral column, comprises the twelve vertebrae between the cervical and lumbar regions. This region is particularly subject to simple stress and fatigue. Muscle discomfort is often treated by the patient making periodic visits to a chiropractor. Relief is usually temporary and requires repeat visits with the attendant cost and inconvenience.

For discomfort in each of these back regions, patients have often resorted to self help, or personal use, hand held back massagers. One such device is manufactured by the Pressure Positive Company 128 Oberholtzer Road, Gilbertsville, Pa. 19525. This device has a small knob at each end of a stiff rod bent in an S-shape. The patient positions one knob on the back while pulling the other knob at the opposite end of the rod. The knob in contact with the back, or the dorsal surface of the patient, is leveraged by the S-shape of the rod when pulled over the shoulder, or around the thoracic or lumbar areas, to apply pressure to the back. Another hand held device for massaging the back is disclosed in U.S. Pat. No. 4,590,926 issued May 27, 1986. This is a flexible, palm held plastic massager notched at one end. Two projections on either side of the notch are manipulated down the vertebral column. These massagers and similar devices are not believed to function with lasting effect, nor do they provide a true physiotherapy method that effectively deals with the variety of causes of back pain reducing or eliminating the need for visits to a chiropractor or physician.

SUMMARY OF THE INVENTION

The present invention provides an apparatus and method for physiotherapy in which the therapy apparatus comprises a straight portion positionable around the body with a forwardly directed near distal end and rearwardly directed front distal end. An elastomeric, divergent contact element on the rear distal end is axially engageable with the dorsal surface, or back, of the patient in the region to receive therapy.

The therapy method comprises gripping the straight portion with one hand and simultaneously pushing on the front distal end with the opposite hand producing a controlled axially directed therapeutic reaction force yieldably transmitted through the elastomeric divergent contact element on the rear distal end to act upon precise paraspinalis muscles undergoing stress.

The invention further resides in the physiotherapeutic treatment of weakened limbs, or in assisting flexion and extension, and in exercising the musculoskeletal body whether in the standing, seated or prone position for those suffering from permanent or partial loss of mobility of standard body movements and comprises the steps of lifting a part of the body with one distal end of the apparatus while applying a reaction force either axially or rotationally to the opposite distal end so as to impart the degree of flexion or extension desired in exercising the body member.

The method includes grasping the straight portion with either hand, and simultaneously or alternately, applying a yieldable torsional pressure to the divergent contact element by rotating the straight portion while pushing axially with the opposite hand on the front distal end. Selected locations on the dorsal surface are reached controlled therapy of the paraspinalis muscles of the back is achieved.

A principal object of the invention is the effective relief of low back syndrome by a therapy apparatus obviating the need for frequent visits to professionals.

Another object of the invention is to provide a device for exercising to restore standard body movement, flexion to disabled or partially disabled limbs, and strengthening by reaction forces graduated or controlled by the patient.

These and other objects will be more apparent by reference to the preferred embodiment of the invention as set forth in the detailed description and by reference to the drawings in which the best mode of the invention is described by way of example with reference to the accompanying figures.

DETAILED DESCRIPTION OF THE INVENTION

Figure 2:
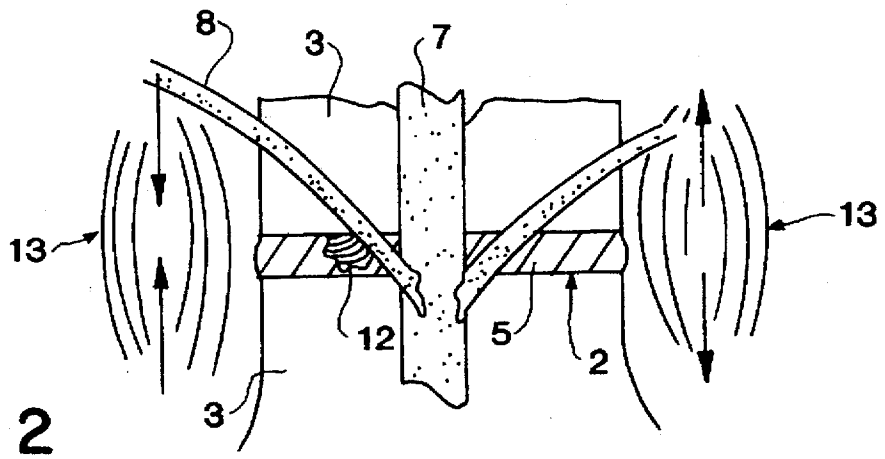
FIG. 2 is a partial vertical sectional view below the dorsal surface in FIG. 1 showing the spasms of the paraspinalis muscles relieved by the therapy method according to the invention.

The weight bearing and shock absorbing characteristics of the human spine, or vertebral column (1), requires an understanding of the musculoskeletal structure. The discs (2) are captured between the vertebrae (3). Each disc has a fibrous bag (4) with a jelly like center, the nucleus pulposus, held by the annulus fibrosis, or tough fibrous outer covering (5). The posterior longitudinal ligament (6) prevents the disc from spreading backwards under compression loading on the spine where it could impinge upon the spinal chord (7) or more likely the nerve root endings (8) which extend from the spinal canal (9) through the neural foramen or windows at the sides of the vertebrae (3). The discs (2) are also captured at the front of the spine by the anterior longitudinal ligament (10). When the annulus fibrosis (5) distends rearwardly or protrudes in one area, as depicted at (12) in FIG. 2 it may cause the anterior ligament (6) to impinge upon a nerve root ending (8) causing spasms, as depicted by the arrows running in opposite directions in FIG. 2, in the paraspinalis muscles, or the large back muscles (13) on opposite sides of the vertebral column. The protrusion at (12) causes pressure on the tissues adjacent to the nerve root endings (8) producing a syndrome known as herniated nucleus pulposus (HNP). This is one of the causes of low back syndrome when it occurs in the lumbar region of the spine. The muscles (13) try to rotate the nerve root endings (8) away from the protrusion by contraction or extension on opposite sides of the spine. This can result in the spine being visibly distorted. The spasms themselves may be painful, but may act to take pressure off of the nerve endings by opening up the intervertebral disc space on the side opposite the muscle spasm. Other peripheral HNP are relieved by spasm on the same side by moving the nerve root endings away from the herniated portion.

In accordance with a preferred embodiment of the invention, a therapy apparatus (15) has a first, or front distal end (18) extending rearwardly, directly facing the ventral surface of the patient's body. By anatomical convention, if the patient is standing facing us, the end (18) is displaced from the sagittal section, or the vertical plane front to back, through the vertebral column, to the left side. A second, or rear distal end (20) extending forwardly faces the dorsal surface of the patient. It is displaced to the left of the sagittal section a lesser extent than the end (18), preferably about an inch, to inch and a half, or up to two inches. A straight portion (24) connects the ends (18) (20) forming a rigid elongated loop bar with radial bends at each end terminating in the respective distal ends defining a gap on one side of the loop formed by the bar. The bar is about 30 to 36 inches long, preferably about 32½ inches in overall length. The front distal end radius is about 3 to 4 inches, preferably 3½ inches, and the rear distal radius of about 4 to 6 inches, preferably 5 inches. The two ends are in the same transverse plane with the straight portion being spaced approximately 20–25 inches apart. The rigid straight portion (24) has a grip, or sleeve (26), surrounding it, shown partially broken away in FIG. 1, on which one hand of the patient is positioned for rotating the bar and for precisely locating the rear distal end over the dorsal surface.

The rear distal end carries an elastomeric, divergent, therapeutic contact element (28) which is yieldable in the axial, radial and torsional directions. The contact element (28) is a highly flexible elastomer approximately an inch to inch and one half deep axially, and approximately the same in diameter. By pressing and rotating the contact element (28) against the dorsal surface, the paraspinalis muscles (13) below respond to the reaction forces radiating into the deep musculoskeletal area adjacent to the spine to set up nerve impulses counteracting those causing spasms, as depicted by the directional arrows in FIG. 2. The patient may precisely locate the contact element (28) on the dorsal surface where the pain seems to be emanating. By applying torsional and axial forces rhythmically, or just by an axial force alone, reaction forces are imparted that counteract the muscle forces causing pain reducing or relieving the discomfort. The contact element (28) may be varied in size, or the degree of flexibility in either compression or torsion may be varied according to the degree of softness required by the muscle tone or age of the patient.

According to the preferred therapy method, the straight portion (24) is grasped to position the contact element (28) against the dorsal surface while the patient pushes on the front end (18) with one hand. The straight portion (24) may at the same time be rotated up and down producing the desired combined reaction forces at the rear end (20) which are imparted through the contact element (28). The reaction forces may be pulsating axial forces, a rhythmic, steady or, combined torsional and axial force, as controlled by the patient. Stress and attendant pain associated with musculoskeletal abnormality, HNP, or radicular pain shooting down the leg, which is the classic symptom of a ruptured disc or sciatic pain, or just plain fatigue, are relieved.

Figure 1:
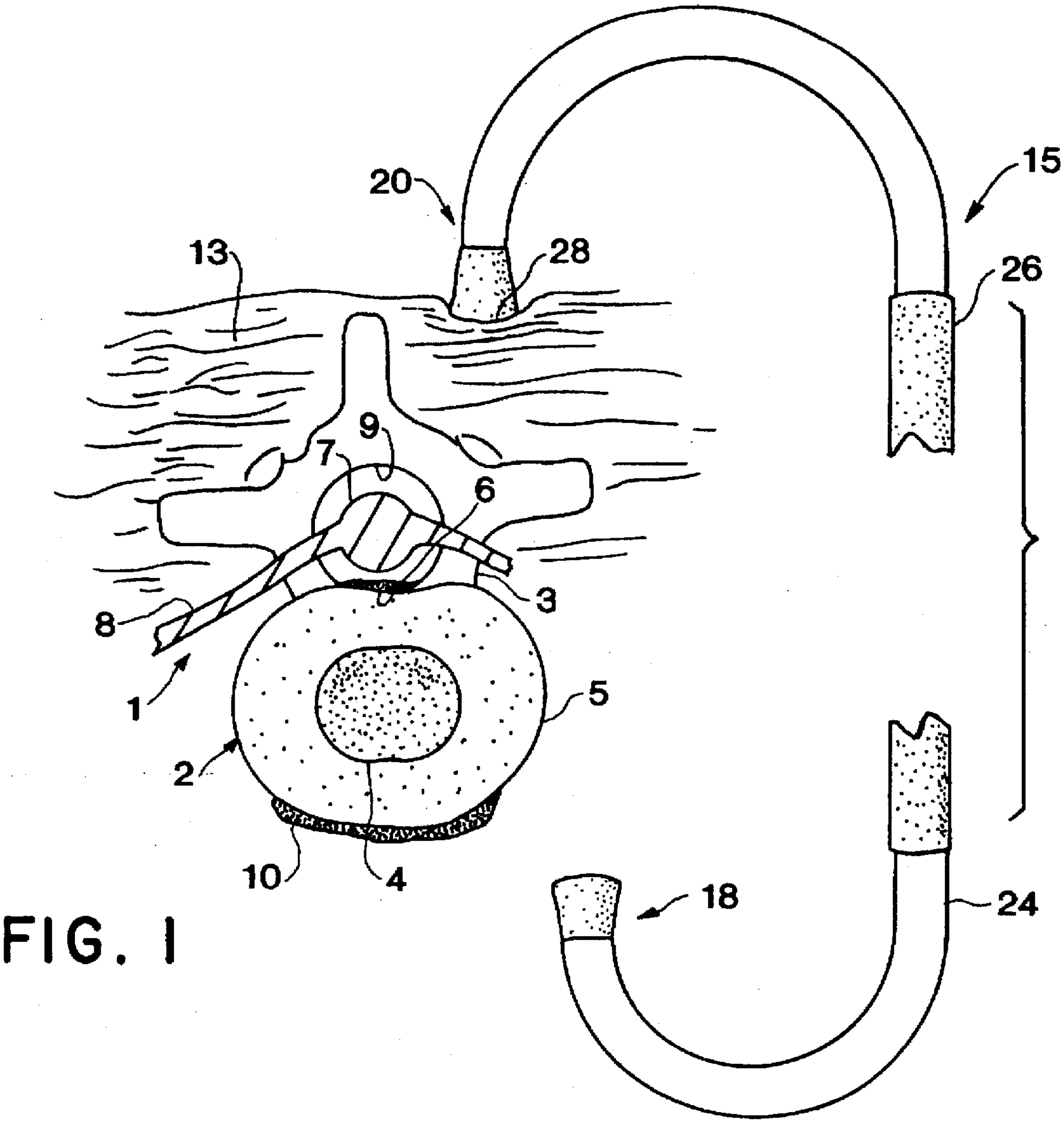
FIG. 1 is a transverse sectional view of a part of the vertebral column showing the straight portion, partially broken away, of the therapy apparatus on the left side of the patient with the rear distal end on the dorsal surface radiating reaction force axially into the paraspinalis muscles below relieving their spasms depicted by the directional arrows in FIG. 2.

The apparatus may be used with the contact element (28) moved along the cervical spine area, the thoracic area, or the lumbar spine depicted in FIG. 1. The apparatus may also be used as an exerciser of the feet, legs, and arms by placing the limb in the curved portion terminating in the distal end (20) and pulling or rotating on the curved portion terminating in the distal end (18), or other areas such as the bottoms of the feet may be massaged by the contact element (28). In addition to this flexion or extension of the limbs, which may be strengthened by exercise, impaired mobility of a partially paralyzed limb can be restored to something like standard flexion by using the apparatus and method of physiotherapy according to the invention as defined in the appended claims.

I claim:

1. A physiotherapy apparatus comprising:

an elongated loop member having an opening on one side, said loop member having a first distal end portion on one end of the loop member and, a second distal end portion on an opposite end of the loop member, said distal end portions facing in opposite directions creating said opening between the distal end portions, said loop member having a straight side portion rigidly interconnecting the first and second distal end portions, the length of which is such that the gap between the two distal end portions is large enough to allow partial encirclement of the human musculoskeletal structure in the opening of the loop member, said first distal end portion bending from said straight side portion to a lesser extent than said second distal end portion creating a smaller one end of said loop member than said opposite end of the loop member, said straight side portion having a portion of its length defining a hand hold for gripping the apparatus and positioning said first and second distal end portions after partial encirclement of the human musculoskeletal structure in said opening of the loop member, said gap between the said two distal end portions being approximately equal to the length of said hand hold portion, and said distal end portions being formed on a radius of curvature extending from said straight side portion in which said first distal end portion has a radius of curvature of between three and four inches while the said second distal end portion has a radius of curvature of between four and six inches whereby any combination of manipulative or acupressure therapeutic actions may be applied to any portion of the musculoskeletal structure.

2. A physiotherapy apparatus as set forth in claim 1 wherein the first and second distal end portions are spaced apart about 20–25 inches.

* * * * *